United States Patent [19]
Alba et al.

[11] Patent Number: 5,634,901
[45] Date of Patent: Jun. 3, 1997

[54] METHOD OF USING A CATHETER SLEEVE

[75] Inventors: Paul Alba, Cupertino; Enrique J. Klein, Los Altos, both of Calif.

[73] Assignee: Localmed, Inc., Palo Alto, Calif.

[21] Appl. No.: 325,958

[22] Filed: Oct. 20, 1994

Related U.S. Application Data

[63] Continuation-in-part of Ser. No. 222,143, Apr. 1, 1994, Pat. No. 5,571,086, and Ser. No. 305,250, Sep. 13, 1994, Pat. No. 5,536,250, which is a continuation-in-part of Ser. No. 221,613, Apr. 1, 1994, abandoned, said Ser. No. 222,143, is a continuation-in-part of Ser. No. 47,737, Apr. 15, 1993, Pat. No. 5,336,178, which is a continuation-in-part of Ser. No. 969,595, Nov. 2, 1992, abandoned.

[51] Int. Cl.$^6$ .................................................. A61M 29/00
[52] U.S. Cl. .................................................. 604/96; 606/194
[58] Field of Search ................ 604/96, 101; 606/191, 606/192, 194

[56] References Cited

U.S. PATENT DOCUMENTS

| | | |
|---|---|---|
| 1,762,858 | 6/1930 | Freeman . |
| 2,499,045 | 2/1950 | Walker . |
| 3,173,418 | 3/1965 | Baran . |
| 3,428,046 | 2/1969 | Remer . |
| 4,403,612 | 9/1983 | Fogarty . |
| 4,417,576 | 11/1983 | Baran . |
| 4,423,725 | 1/1984 | Baran . |
| 4,704,130 | 11/1987 | Gilding . |
| 4,710,181 | 12/1987 | Fuqua . |
| 4,738,666 | 4/1988 | Fuqua . |
| 4,744,366 | 5/1988 | Jang . |
| 4,813,966 | 3/1989 | Gilding . |
| 4,820,349 | 4/1989 | Saab . |
| 4,963,313 | 10/1990 | Noddin . |
| 5,049,132 | 9/1991 | Shaffer . |
| 5,102,390 | 4/1992 | Crittenden et al. ............ 604/96 |
| 5,116,318 | 5/1992 | Hillstead ....................... 604/96 |
| 5,135,516 | 8/1992 | Sahatjian . |
| 5,176,638 | 1/1993 | Don Michael . |
| 5,178,608 | 1/1993 | Winters . |
| 5,180,366 | 1/1993 | Woods . |
| 5,195,969 | 3/1993 | Wang . |
| 5,211,654 | 5/1993 | Kaltenbach . |
| 5,226,889 | 7/1993 | Sheiban . |
| 5,254,089 | 10/1993 | Wang . |
| 5,257,974 | 11/1993 | Cox . |
| 5,282,785 | 2/1994 | Shapland . |
| 5,295,962 | 3/1994 | Crocker . |
| 5,304,120 | 4/1994 | Crandell . |
| 5,304,121 | 4/1994 | Sahatjian . |
| 5,318,531 | 6/1994 | Leone . |

(List continued on next page.)

FOREIGN PATENT DOCUMENTS

WO 92/17221 10/1992 WIPO .
WO 95/03083 2/1995 WIPO .......................... A61M 31/00

OTHER PUBLICATIONS

Polysciences, Inc. Data Sheet #365 on Biodegradable Polymers, Jan. 1990.
Medisorb Technologies International L.P., pp. 7 and 9, describing controlled release of bioactive materials.

*Primary Examiner*—Corrine M. McDermott
*Attorney, Agent, or Firm*—Townsend and Townsend and Crew LLP

[57] ABSTRACT

A balloon catheter assembly (2) includes a catheter (8) having a catheter shaft (10) with a balloon (12) at its distal end. A sleeve assembly (16) has a diametrically expanding balloon enlargement sleeve (18) at its distal end sized to be positionable over the balloon when the balloon is deflated. The enlargement sleeve can expand from a relaxed condition, at which it is placed over the deflated balloon, to an expanded condition surrounding the fully inflated balloon. The enlargement sleeve is sufficiently thick when expanded for an enlarged dilatation of the vessel when the balloon is reinflated. The enlargement sleeve can be made of elastic or substantially inelastic material; it can also include a porous matrix material with a drug interspersed therein so the drug is applied topically when the vessel is redilated.

28 Claims, 3 Drawing Sheets

U.S. PATENT DOCUMENTS

| | | |
|---|---|---|
| 5,324,261 | 6/1994 | Amundson . |
| 5,336,178 | 8/1994 | Kaplan . |
| 5,338,300 | 8/1994 | Cox . |
| 5,342,348 | 8/1994 | Kaplan . |
| 5,364,356 | 11/1994 | Höfling . |
| 5,425,709 | 6/1995 | Gambale . |
| 5,439,445 | 8/1995 | Kontos ................................. 604/96 |

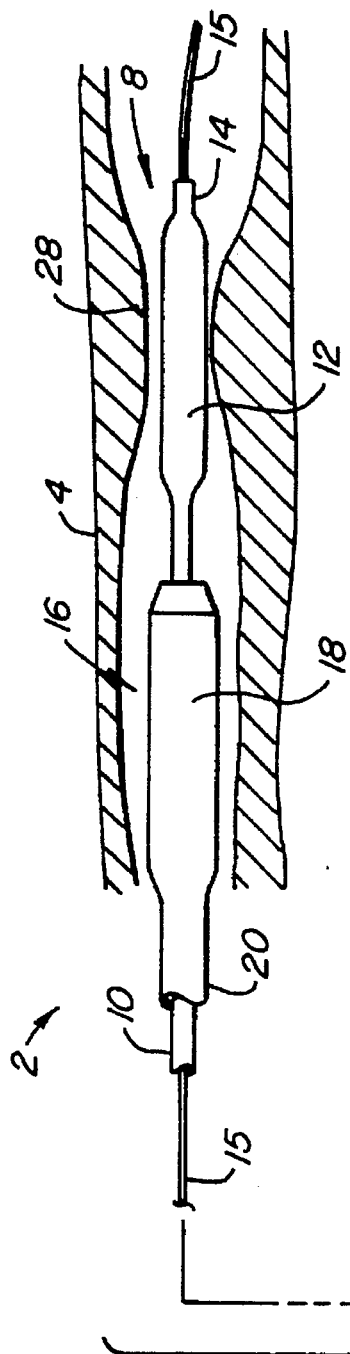
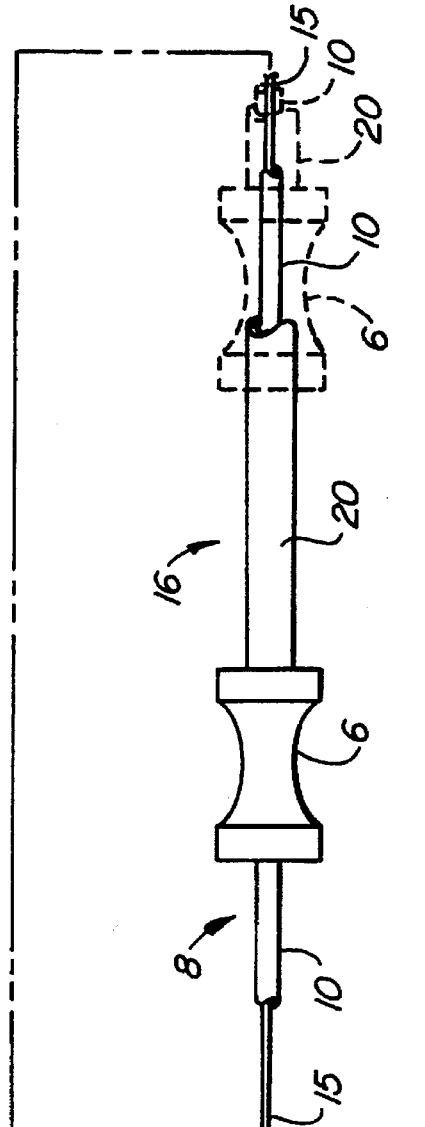
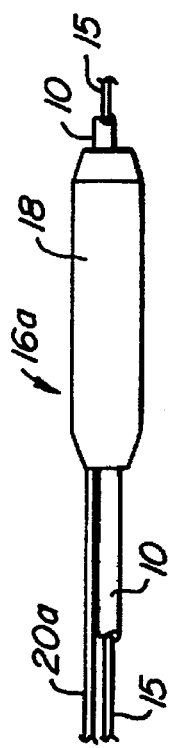
FIG. 1.
FIG. 4.

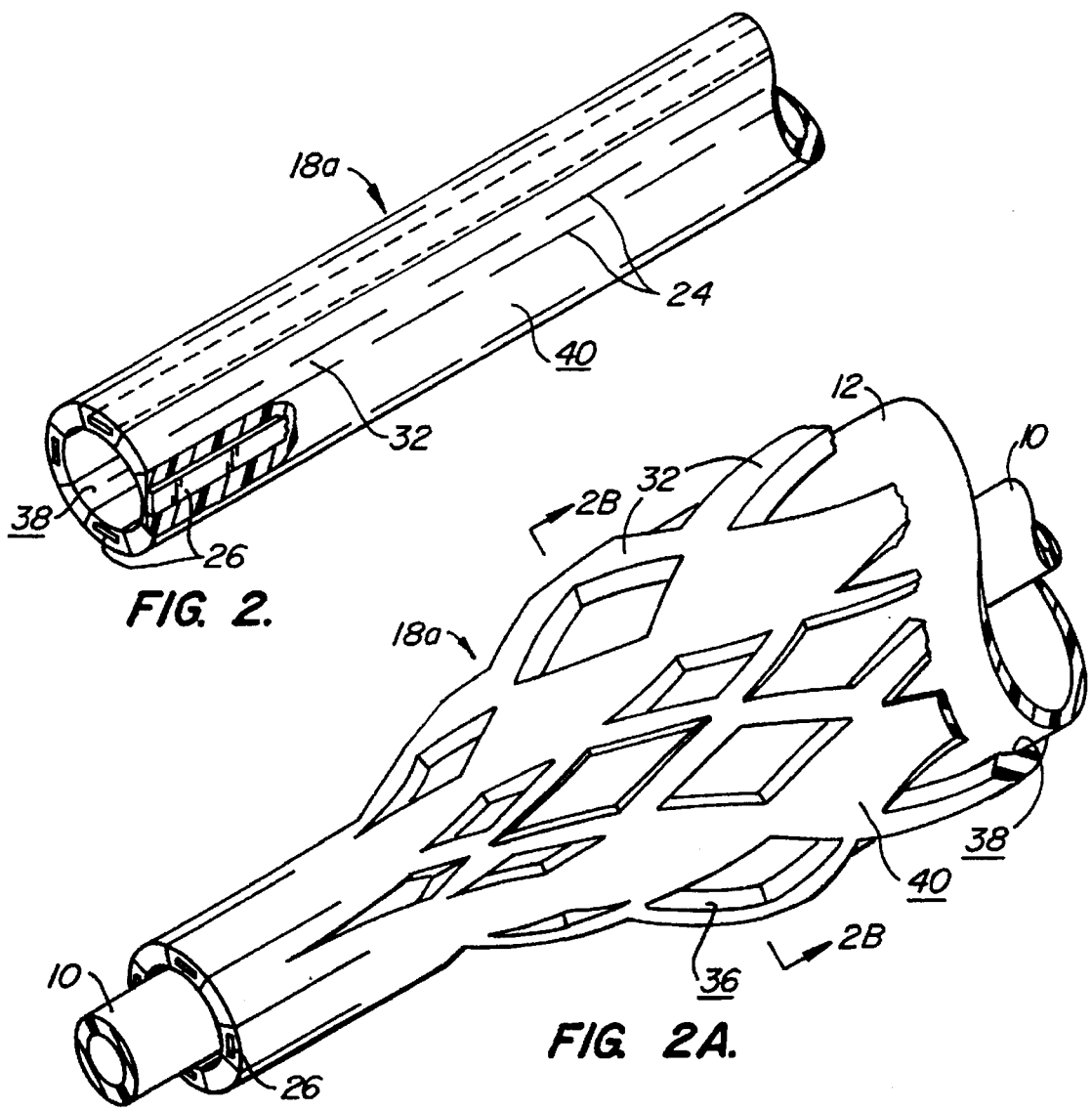
FIG. 2.
FIG. 2A.
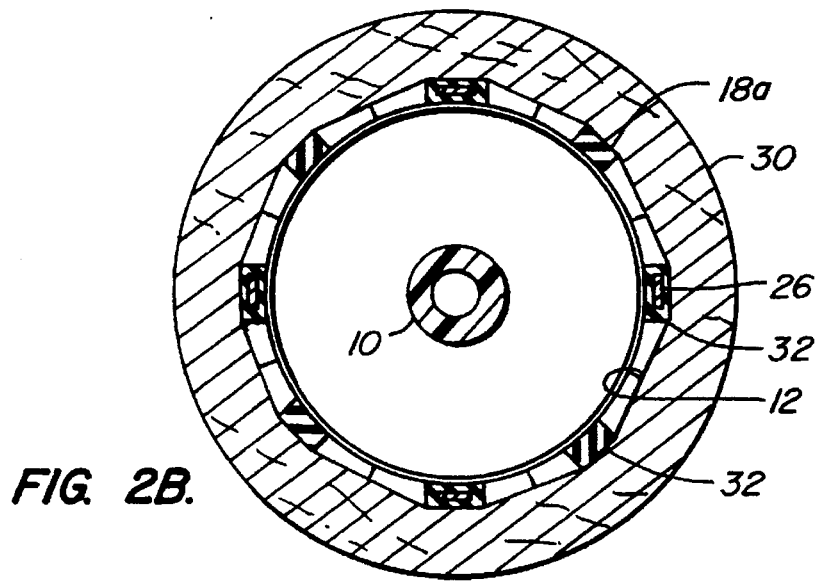
FIG. 2B.

METHOD OF USING A CATHETER SLEEVE

CROSS-REFERENCE TO RELATED APPLICATION

This application is a continuation-in-part of application Ser. No. 08/222,143, filed Apr. 1, 1994, now U.S. Pat. No. 5,571,086 which was a continuation-in-part of application Ser. No. 08/047,737, filed on Apr. 15, 1993, now Pat. No. 5,336,178, which was a continuation-in-part of application Ser. No. 07/969,595, filed on Nov. 2, 1992, now abandoned, the complete disclosures of which are incorporated herein by reference. This application is also a continuation-in-part of application Ser. No. 08/305,250, entitled Perfusion Shunt Device and Method, filed on Sep. 13, 1994, now U.S. Pat. No. 5,536,250, which was a continuation-in-part of application Ser. No. 08/221,613, filed on Apr. 1, 1994, now abandoned, the full disclosures of which are incorporated herein by reference. This application is related to U.S. Pat. No. 5,342,348 and application Ser. No. 08/241,428 filed May 11, 1994, the full disclosures of which are incorporated herein by reference.

BACKGROUND OF THE INVENTION

In percutaneous transluminal angioplasty procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and restore adequate blood flow through the diseased region.

Balloons on conventional angioplasty catheters have low compliance. Therefore, after the balloon is internally pressurized, a further increase of the internal pressure will cause the outside diameter of the balloon to increase only minimally. This prevents the balloon from overexpanding and causing substantial damage to the vessel.

Interventional cardiologists, use on average 1.5 balloon catheters for each procedure. The first catheter used is chosen to have the largest balloon that will cross the stenosis and will also have an inflated diameter of the order of the vessel diameter proximal to the stenosis. Often the diameter of this balloon is smaller than desired in order to cross the lesion. After the first catheter has been expanded, a second catheter is therefore often needed to further dilate the lesion. Typically, the increase in balloon dilatation diameter is 0.5 mm. For example, the first catheter may have a balloon having an expanded diameter of 2.5 mm. In a standard procedure, after the first balloon has been expanded, it is deflated, removed from the patient and a second balloon catheter, typically having a 3.0 mm diameter balloon when expanded, is introduced to the lesion. The balloon is then positioned at the region of stenosis and expanded to its full diameter to further dilate the vessel to the proper size. Since dilatation balloon catheters are designed for single use only and since they are expensive, presently about U.S. $300 to U.S. $800 each, the use of two balloon catheters for each procedure substantially increases the cost of the procedure. Use of two balloon catheters in sequence also increases the length of the procedure.

At times it is desired to deliver a therapeutic agent, typically a drug, to a target site through a body lumen such as an artery, vein or other hollow organs of the gastrointestinal, genitourologic or pulmonary systems. One way to deliver a drug to a target site along the wall of a body passage or lumen is disclosed in U.S. Pat. No. 5,304,121 to Sahatjian. It shows a dilatation balloon catheter in which the balloon is coated with a hydrogel polymer layer incorporating a drug in aqueous solution. Upon expansion of the balloon the drug is released to the wall of the body lumen at the target site. This method has its drawbacks and limitations. Hydrogel layers can contain only a limited amount of drug and the drug tends to diffuse quickly out of the hydrogel where it is subject to being washed away by the blood stream prior to reaching the target site. Both of these factors can limit the effectiveness of using a hydrogel layer to deliver a drug to a target site.

SUMMARY OF THE INVENTION

This invention relates generally to intravascular dilatation devices, and more specifically to an intravascular sleeve catheter which eliminates the need for the use of a second balloon catheter, where such a second catheter expands to a larger diameter than the first, to definitively dilate a vessel.

The present invention is directed to a balloon catheter assembly and its method of use. The catheter assembly includes a dilatation balloon catheter having a catheter shaft with a balloon at the distal end of the catheter shaft. A sleeve assembly has a radially expanding enlargement sleeve at its distal end sized to be positionable over the balloon of the dilatation catheter when the balloon is in the deflated condition. The enlargement sleeve can expand from a pre-use, relaxed condition, at which it is placed over the deflated balloon, to an in-use, expanded condition surrounding the fully inflated balloon. The enlargement sleeve when in the expanded or in-use condition has a radial thickness sufficient to enhance or enlarge the dilatation of the vessel at the site of the lesion when the balloon of the dilatation catheter is reinflated.

A primary advantage of the invention is that it eliminates the need for using a second costly balloon dilatation catheter to achieve the necessary enlargement of a vessel. The sleeve catheter is simpler in construction and should be much less expensive than a second standard balloon dilatation catheter so that significant monetary savings can be achieved. Also, since replacement or exchange of balloon dilatation catheters is not necessary, the entire procedure can be done more quickly which also represents a cost savings; the balloon from the first and only dilatation catheter is inflated to dilate the target site and then deflated, after which the balloon enlargement sleeve, which can be pre-loaded over the shaft of the dilatation or angioplasty catheter, is aligned over the deflated balloon and the balloon is reinflated so as to expand the target site to the enlarged diameter determined by the inflated diameter of the balloon, which remains the same in both cases, plus twice the radial thickness of the enlargement sleeve. This can increase the speed and lower the cost of the procedure over that of a conventional procedure using two separate balloon dilatation catheters sequentially.

The axial stiffness of the enlargement sleeve necessary to permit it to advance through the lumen and over the dilatation balloon to the target site is preferably provided by one or more axially extending stiffener elements. The stiffener elements preferably have a flattened rectangular cross-sectional shape and are embedded within the wall of the enlargement sleeve. Radiopaque markers can be incorporated into the stiffener elements to assist with the proper alignment of the enlargement sleeve over the balloon of the dilatation catheter.

The enlargement sleeve can be made of an elastomeric or of a substantially inelastic material. In one embodiment the enlargement sleeve is of an elastomeric material, the relaxed thickness of which is chosen so that when aligned with the inflated balloon, the radial thickness of the elastic enlargement sleeve is sufficient to incrementally dilate the vessel. In another embodiment the enlargement sleeve is made of a substantially inelastic material made radially expandable by virtue of a series of slits or other separations which permit the enlargement sleeve to expand radially as the balloon expands. With this type, the thickness of the wall of the enlargement sleeve remains substantially constant and is chosen to provide the additional thickness desired during the re-expansion of the balloon.

Another aspect of the invention is the use of a porous matrix material containing a drug interspersed therein in at least a portion of the region of expansion of the enlargement sleeve. This enables the enlargement sleeve to administer a drug to the target site when the balloon is expanded. An advantage of this aspect of the invention is that no separate drug delivery lumen is needed. Another advantage results from the fact that the enlargement sleeve can be made substantially thicker than the thickness of a hydrogel layer, a conventional method for delivering a drug to a target site. While a hydrogel layer may be on the order of 0.05 mm thick, the enlargement sleeve can be made substantially thicker and even after being expanded over an angioplasty balloon, can be typically from 0.25 to 0.50 mm thick. This is possible since the relaxed thickness of the enlargement sleeve affects the introducing profile of the dilatation balloon only after the original dilatation has taken place, leaving a substantially larger vessel lumen for the reintroduction of the combination dilatation balloon and sleeve. The thicker porous matrix material, which is typically made from an elastomeric material, can be made to absorb or carry substantially more drug usually up to 100 times more than the 10 to 30 milligrams of drug usually carried by a conventional hydrogel layer. Also, drug in a hydrogel layer is subject to being substantially washed away by the flow of blood around this hydrogel layer prior to dilatation. The drug in the porous matrix material may be retained better than in the hydrogel layer because the bulk of the drug is well below the surface of the matrix, and the porous matrix can be engineered to have smaller pores on its outer surface. Other losses of the drug in the porous matrix material, typically through a decrease in the thickness of the porous matrix material during expansion of the balloon can be minimized by providing longitudinal slits in the porous matrix and sealing off the walls of the slits, or, the drug interspersed within the porous matrix material can be contained in microcapsules which rupture and release the drug only when the porous matrix comes in contact with the vessel wall and the balloon applies additional pressure on the constrained porous matrix. Additionally, bioabsorbable particles comprising drugs dispersed in polyglycolic/polylactic acid matrices can be distributed within the porous matrix. When the balloon is inflated and the porous matrix sleeve becomes squeezed between the balloon and the inner surface of the body lumen, these granules will be forced into the tissue at the target site.

Other features and advantages of the invention will appear from the following description in which the preferred embodiments have been discussed in detail in conjunction with the accompanying drawings.

BRIEF DESCRIPTION OF THE DRAWINGS

FIG. 1 is a simplified side view showing a catheter assembly including a dilatation balloon catheter and an elastomeric enlargement sleeve with the dilatation balloon positioned at a region of stenosis within a blood vessel prior to inflation of the balloon;

FIG. 2 is an enlarged view of the distal end of an enlargement sleeve assembly with a substantially inelastic enlargement sleeve in a relaxed condition illustrating longitudinal stiffener elements and radially extending slits in the enlargement sleeve;

FIG. 2A illustrates the enlargement sleeve of FIG. 2 having the catheter shaft therein and the dilatation balloon inflated so as to place the enlargement sleeve in its expanded condition similarly to FIG. 1C;

FIG. 2B is a cross-sectional view taken along line 2B—2B of FIG. 2A with the addition of a vessel being dilated over the enlargement sleeve;

FIG. 4 is a partial side view of an alternative embodiment of the sleeve assembly of FIG. 1.

DESCRIPTION OF A FIRST PREFERRED EMBODIMENT

Figure 1A:
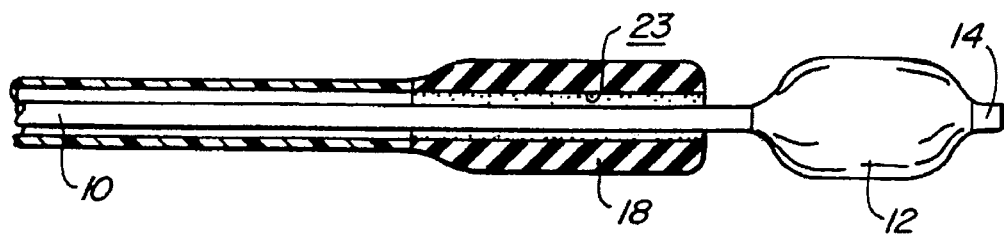
FIGS. 1A, 1B and 1C show the balloon catheter assembly of FIG. 1 with the balloon inflated in FIG. 1A, with the balloon deflated and the relaxed enlargement sleeve advanced to a distal position overlying the balloon in FIG. 1B, and with the balloon inflated and enlargement sleeve expanded so the thickness of the enlargement sleeve provides an additional radial expansion of the region of stenosis resulting in a two-stage dilatation of the region.

FIG. 1 illustrates, in simplified form, a catheter assembly 2 showing the distal end within a blood vessel 4. Assembly 2 includes a proximal end fitting 6 through which a dilatation balloon catheter 8 passes. Balloon catheter 8 includes a catheter shaft 10 and a dilatation balloon 12 at the distal end 14 of catheter shaft 10. A guide wire 15 is used within catheter shaft 10.

Figure 1B:
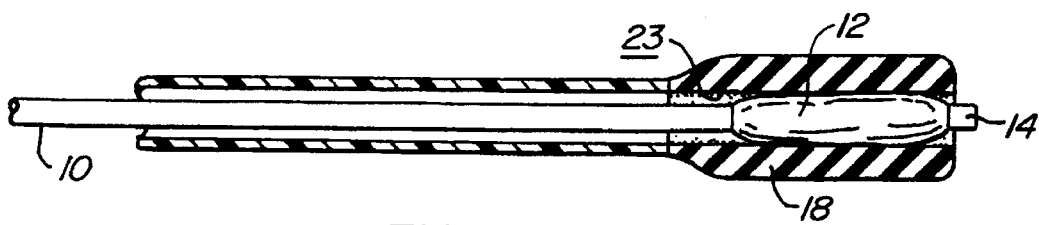
Figure 1C:
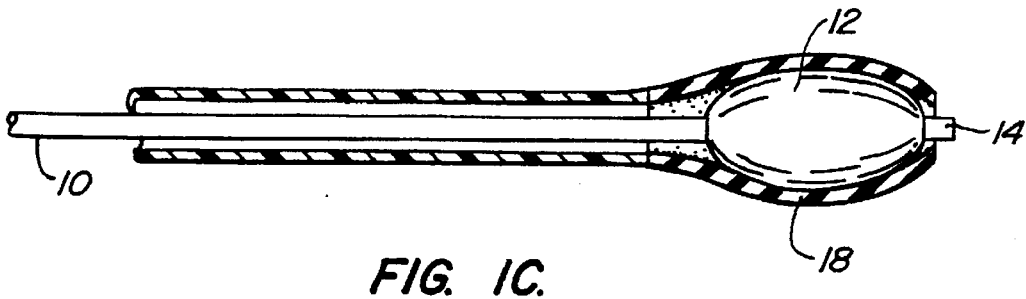

A tubular sleeve assembly 16 is slidably mounted over catheter shaft 10. In the embodiment of FIG. 1, sleeve assembly 16 includes tubular, radially expandable, elastomeric enlargement sleeve 18 at the distal end of sleeve assembly 16 and a connecting tube 20 coupling enlargement sleeve 18 to proximal end fitting 6. The thickness of enlargement sleeve 18 is exaggerated in FIGS. 1A–1C. Movement of fitting 6 from the solid line position to the dashed line position of FIG. 1 causes enlargement sleeve 18 to move from the position of FIG. 1 to the position of FIG. 1B as discussed below.

In a first preferred embodiment, dilatation balloon catheter 8 is of a conventional design having a low compliance dilatation balloon 12. Tubular sleeve assembly 16 could be made from an elastomeric material, such as a medical grade synthetic rubber, Santoprene® (Advanced Elastomeric Systems) or a thermoplastic elastomeric polyurethane sold under the trademark Tecoflex® by Thermedics, Inc. or Kraton® by Shell Chemical Co. However, the radially expandable enlargement sleeve 18 is preferably fabricated as a separate component, including its own axially extending stiffeners, and then thermally, mechanically or otherwise bonded to a connecting tube 20 using conventional methods; connecting tube 20 would preferably be made of a conventional biocompatible, relatively inelastic but flexible material, such as Pebax®, polyester or polyethylene. The joint between enlargement sleeve 18 and its associated connecting tube, not shown, can be made in a variety of ways, such as by overlapping inner and outer portions of the sleeve and connecting tube to create a good joint using adhesives, should thermal bonding prove impractical.

To provide appropriate longitudinal stiffness for enlargement sleeve 18 so it may be maneuvered into position over dilatation balloon 12 without collapsing, axially extending stiffeners 26, see FIG. 2, are incorporated into enlargement sleeve 18. Stiffeners 26 are preferably made of stainless steel but can also be made of a superlastic nickel titanium alloy called Nitinol, and are approximately 40 mm long, with a rectangular cross section to fit within the wall of the enlargement sleeve. Alternatively, they may also be made with round, elliptical, oval or other cross sectional shapes. Stiffeners 26 will typically extend into connecting tube 20 about 5–10 mm. It is preferable that stiffener elements 26 used with enlargement sleeve 18 extend across the joint between the enlargement sleeve and the connecting tube to improve the joint strength.

To assist proper axial alignment of enlargement sleeve 18 with balloon 12, radiopaque markers may be provided on the distal portion of catheter assembly 2. Preferably radiopaque markers are disposed on one or more of stiffeners 26. Markers are formed by, for example, plating a radiopaque material such as gold or platinum onto stiffeners 26. Dilatation balloon catheter 8 will also have a radiopaque marker typically in the form of a gold or platinum band on catheter shaft 10 adjacent balloon 12. In one embodiment, two markers are disposed on at least one stiffener 26, the markers being separated a distance from one another usually about equal to or slightly greater than the length of the marker on catheter shaft 10. In this way, by visualization through radiographic imaging, the markers on stiffener 26 facilitate axial alignment of enlargement sleeve 18 with balloon 12 by aligning the marker on catheter shaft 10 between the markers on stiffeners 26. The markers further provide visual indication of the location of balloon 12 within vessel 4 so that balloon 12 may be positioned adjacent to a treatment site. Other arrangements of radiopaque markers can be used as well, such as disclosed in U.S. Pat. No. 5,336,178 and in co-pending application Ser. No. 08/241,428.

FIGS. 1A–1C illustrate the distal portion of catheter assembly 2 in simplified form during its use. FIG. 1A shows catheter assembly 2 in the same position as shown in FIG. 1 but with balloon 12 expanded to dilate target area 28 at the region of stenosis. After dilatation balloon 12 is deflated, proximal end fitting 6 is moved from the solid line position to the dashed line position of FIG. 1. This drives enlargement sleeve 18 over the deflated dilatation balloon 12 as shown in FIG. 1B. Dilatation balloon 12 is then re-expanded, thus expanding enlargement sleeves 18 or 18a as shown in FIGS. 1C and 2A. The diameter of dilatation balloon 12 is the same in FIGS. 1A and 1C. However, the effective diameter of catheter assembly 2 at target area 28 is increased by the expanded thickness of elastomeric enlargement sleeve 18 or the substantially constant thickness of enlargement sleeve 18a. This permits the incremental enlargement of a region of stenosis 28 by a known predetermined value. This also eliminates the need to remove balloon catheter 8 after expanding balloon 12 and replacing balloon catheter 8 with another balloon catheter having a dilatation balloon which expands to a larger diameter. The present invention not only saves time, it can also save money since sleeve assembly 16 should be less expensive to manufacture than a balloon catheter 8.

It is clear that when the expandable enlargement sleeve 18 is made of an elastomeric material, the initial relaxed wall thickness of this sleeve will decrease as it is expanded by the underlying balloon 12 of the dilatation balloon catheter 8.

Figure 3:
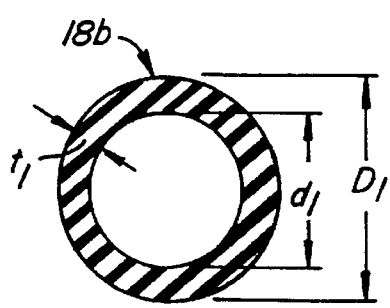
FIG. 3 shows a cross-sectional view of an elastomeric enlargement sleeve in a relaxed condition.
Figure 3A:
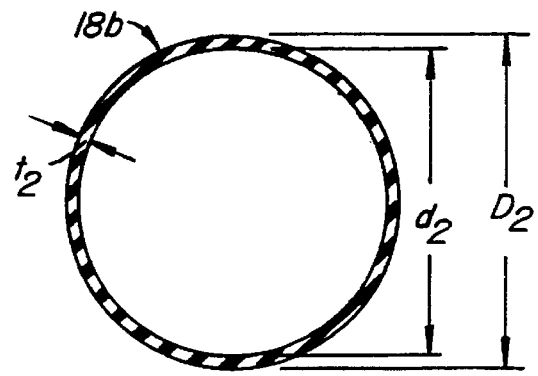
FIG. 3A illustrates the enlargement sleeve of FIG. 3 in an expanded condition showing how the wall thickness decreases during expansion.

FIG. 3 illustrates a cross-sectional view showing an elastomeric enlargement sleeve 18b in a relaxed state. As shown in FIG. 3, in this state enlargement sleeve 18b has an outside diameter $D_1$, and an inside diameter $d_1$ and a wall thickness $t_1$. Upon expansion as shown in FIG. 3A, the outside diameter, the inside diameter and the wall thickness for enlargement sleeve 18b are labelled $D_2$, $d_2$ and $t_2$ respectively. Assuming that longitudinal contraction of the enlargement sleeve is minimal during expansion, the cross-sectional area will remain essentially constant. For known values of $d_1$, $d_2$ and a desired wall thickness $t_2$, an algebraic expression for the initial wall thickness $t_1$ can be derived as:

$$t_1 = \frac{-d_1}{2} \pm \sqrt{\left(\frac{d_1}{2}\right)^2 + t_2(t_2 + d_2)}$$

As an example, assuming $t_2$ equals 0.25 mm and $d_1$ equals 1.27 mm (0.05 inch), the following values of $t_1$ are obtained as a function of $d_2$: when $d_2$ equals 2.0, 2.5, 3.0 and 3.5 mm, $t_1$ equals 0.35, 0.41, 0.47 and 0.52 mm, respectively.

The inside surface 23 of elastomeric enlargement sleeve 18 is a lubricous surface to help sleeve 18 slide onto and off of balloon 12. The outside surface of elastomeric sleeve 18 is also lubricious.

Sleeve 18 is preferably made so that it has a uniform thickness when in its relaxed condition of FIGS. 1, 1A and 1B, and a uniform, although reduced, thickness when in the expanded condition of FIG. 1C. To exhibit a uniform radial thickness when sleeve 18 is in the expanded condition, the sleeve thickness should not vary more than about ±10% from the average thickness.

FIG. 4 illustrates an alternative embodiment of the sleeve assembly 16 of FIG. 1. Sleeve assembly 16a is like sleeve assembly 16 but instead of using a connecting tube 20, which surrounds catheter shaft 10, a connecting rod 20a, which lies parallel to but does not surround shaft 10, is used. Rod 20a can be solid, hollow, or of other construction.

The wall thickness of enlargement sleeve 18 for intravascular use is preferably about 0.25 to 0.50 mm when expanded. Depending on the balloon size used, this will typically provide a diametral expansion in the range of 110 to 140%.

In use, balloon catheter 8 is positioned with dilatation balloon 12 deflated at target area 28, typically a region of stenosis. This is usually accomplished with the aid of a guide wire 15, as is conventional. While sleeve assembly 16 could be placed into the position of FIGS. 1 and 1A after balloon catheter 8 alone has been deployed and then withdrawn from the patient's body, sleeve assembly 16 is preferably inserted into blood vessel 4 along with the initial placement of balloon catheter 8 within the blood vessel. Balloon 12 is then inflated to dilate region of stenosis 28 as suggested in FIG. 1A. Balloon 12 is then deflated and proximal end fitting 6 is moved from the solid line position to the dashed line position of FIG. 1 to move enlargement sleeve 18 over dilatation balloon 12 as suggested in FIG. 1B. However, catheter shaft 10 could also be pulled proximally to position deflated dilatation balloon 12 within enlargement sleeve 18; both balloon 12 and sleeve 18 would then be pushed distally into position at the region of stenosis 28. In either event, balloon 12 is then reinflated to the condition of FIG. 1C with enlargement sleeve 18 surrounding the dilatation balloon so as to provide an additional enlargement at, and optionally apply a drug to target area 28 as later described in a third preferred embodiment.

Sometimes it may not be necessary to follow all the steps above when target area 28 does not require the two-step dilatation procedure of FIGS. 1–1C. In such case, the user could, for example, position deflated dilatation balloon 12 at the target area 28 as shown in FIG. 1, move enlargement sleeve 18 over the deflated dilatation balloon and then inflate the dilatation balloon to the condition of FIG. 1C. This may prove especially useful when applying a drug to target area 28 as preventive therapy.

DESCRIPTION OF A SECOND PREFERRED EMBODIMENT

Enlargement sleeve 18a, see FIGS. 2–2B, is created from an extension of connecting tube 20 and has a pattern of axially extending slits 24 which permit enlargement sleeve 18a to expand radially when dilatation balloon 12 is inflated with the enlargement sleeve positioned over the dilatation balloon. The radial thickness of enlargement sleeve 18a is preferably about 0.25 mm and may be of a different thickness than that of connecting tube 20. For a 20 mm long balloon, enlargement sleeve 18a is about 30 mm long and has a number of offset slits 24 to permit sleeve 18a to expand radially over balloon 12 as shown in FIG. 2A.

In FIG. 2B a vessel 30 is shown in cross section being distended by enlargement sleeve 18a and underlying balloon 12 of dilatation balloon catheter 8. The cross section is taken at line 2B—2B in FIG. 2A. To maximize the dilatation effect of enlargement sleeve 18a, a larger, rather than a smaller, number of offset slits 24 is desirable since the remaining webs 32 between slits 24 act as supports for the vessel tissue, which tends to span the gaps between the webs in an essentially straight manner. The number of offset slits 24, their geometrical arrangement and their length determine the range of expansibility of enlargement sleeve 18a. When such an enlargement sleeve is expanded over a dilatation balloon catheter, the free webs of the enlargement sleeve tend to twist around their own axes. This tendency is not apparent when in use since the free webs are compressively contained between balloon 12 and the tissue of vessel 30.

With sleeve assembly 16, of this second preferred embodiment, the entire sleeve assembly is preferably made of the same material as connecting tube 20. This can eliminate the need for special joining techniques.

DESCRIPTION OF A THIRD PREFERRED EMBODIMENT

Another important aspect of the invention involves the use of a modified elastomeric enlargement sleeve having a porous matrix material containing a drug interspersed therein. Porous matrix materials are materials which have pores, voids or other interconnected openings or regions which can contain other materials, such as liquids, gels, microcapsules or granules. Biocompatible microporous polymeric materials having interconnecting pores of controlled pore size in the range of 0.1 to 100 or more microns, and pore size gradients throughout their thicknesses, have been manufactured both in sheet and tubular form. Examples of these porous matrix materials include Mitraflex™ and Spyroflex™, both tradenames of PolyMedica, Woburn, Mass. which are modified polyurethane formulations manufactured by a liquid extrusion process also involving a phase separation utilizing controlled coagulation techniques. (See U.S. Pat. Nos. 4,704,130 and 4,813,966 incorporated herein by reference.) These materials have already found use in the field of wound dressings and are being tested in the field of vascular grafts.

The drug to be interspersed within the porous matrix material can be in the form of an aqueous solution, or, an aqueous solution contained within microcapsules, or, solid bioabsorbable particles. Microcapsules can be rupturable when externally pressurized. Bioabsorbable particles can be embedded in the vessel tissue by the balloon acting against the catheter sleeve as explained later.

It should be understood that the catheter of the present invention is suitable for delivery of a variety of therapeutic agents including pharmaceuticals, proteins, peptides, nucleotides, carbohydrates, polysaccharides, muccopolysaccharides, simple sugars, glycosaminoglycans and steroids. The present invention facilitates delivery of such agents in a variety of formulations, including aqueous vehicle or liposome. The catheter is further useful for the delivery of viral particles to facilitate gene transfer. The agents delivered may perform in a variety of functions, including antithrombotics, antiplatelets, antimetabolics, growth factor inhibitors, growth promoters, anticoagulants, antimitotics, and antibiotics.

A third preferred embodiment may be constructed either in the form of a continuous porous elastomeric sleeve 18 as shows in FIG. 1–1C or a porous elastomeric sleeve 18a with slits as shown in FIGS. 2–2B. FIGS. 2–2B will be used in describing the slit version of the third embodiment. The technique for cutting the slits would typically involve sealing off the surfaces 36 of the porous matrix material on both sides of the slit. Such a sealing process can be achieved through the use of a heated blade or laser cutting technology. A sealing process would also be used on the inner lumen of sleeve 18a. The drug is preferably introduced to the porous matrix following the final catheter assembly, which includes the slitting and sealing operations. The purpose of providing slits with sealed side surfaces 36 is to minimize the loss of drug during the expansion of enlargement sleeve 18a prior to reaching the interior wall of the vessel in the manner illustrated in FIG. 2B. It will be appreciated that the webs 32 of the porous matrix material will distend and thin out when expanded in the manner of sleeve 18a of FIGS. 2A and 2B due to the elastomeric nature of the material, but not to the same extent as if the sleeve had been kept unslit. This small distension, combined with the sealed inner luminal surfaces 38 and the sealed side surfaces 36 of slits 24, will provide for some, but nevertheless minimal release of drug from the porous matrix material through the surface of sleeve 18a during the expansion of the enlargement sleeve. As the enlargement sleeve 18a is further expanded to contact vessel 30 as shown in FIG. 2B and is squeezed between balloon 12 and the vessel wall, the drug in the porous matrix material is then forced through the outer surface 40 of sleeve 18a and into the tissue of the vessel wall providing the desired therapeutic benefit.

Since the drug is captured within the porous matrix material and not on its outer surface 40, the possibility of a drug washout in the blood stream is minimized.

In the case of the drug being carried in microcapsules within the porous matrix material of an expansion sleeve 18a, the expansion of balloon 12 and the squeezing of the porous matrix material against the inner vessel wall can create sufficient pressure to rupture the microcapsules to allow the contents to be released and forced into the vessel wall.

When the drug is in the form of bioabsorbable particles housed in the porous matrix material, as the porous matrix material of sleeve 18a is squeezed between the expansion balloon 12 and the inner vessel wall, and since the balloon surface is a tough impermeable membrane, the bioabsorbable particles will be forced into the softer vessel tissue where they will become embedded in readiness for their pre-programmed, time release of therapeutic drug.

Other modifications and variation can be made to the disclosed embodiments and methods without departing from the subject of the invention as defined in the following claims. For example, an enlargement sleeve including both an elastomeric, or other elastic material with or without drugs interspersed therein, and a substantially inelastic portion can be used.

What is claimed is:

1. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   wherein an expandable balloon enlargement sleeve is disposed over the balloon catheter during at least the inflating and deflating steps;
   positioning the balloon enlargement sleeve in alignment with the deflated balloon while the balloon remains near the target site; and
   reinflating the balloon so as to expand the enlargement sleeve therewith at the target site to a second diemertal dimension to further dilate the target site substantially immediately following the positioning step;
   wherein the enlargement sleeve has a wall thickness sufficient to make the second diametral dimension at least about 110% of the first diametral dimension.

2. The method of claim 1 wherein the inserting step is carried out within the lumen of a blood vessel.

3. The method of claim 1 wherein the sleeve is elastic.

4. The method of claim 1 wherein the sleeve is effectively inelastic.

5. The method of claim 1 wherein the inserting step is carried out by simultaneously inserting both the balloon catheter and the balloon enlargement sleeve therewith into the body lumen.

6. The method of claim 5 wherein the simultaneously inserting step is carried out with the balloon distal to the enlargement sleeve.

7. The method of claim 5 wherein the simultaneously inserting step is carried out with the balloon aligned with the enlargement sleeve.

8. The method of claim 1 wherein the positioning step is carried out by moving the enlargement sleeve relative to the balloon catheter.

9. The method of claim 1 wherein the sleeve has a wall thickness of about 0.25 to 0.50 mm when expanded.

10. The method of claim 1 wherein the sleeve has numerous axial openings formed therein to facilitate diametral expansion of the enlargement sleeve.

11. The method of claim 1 wherein the enlargement sleeve is made of an elastomeric material.

12. The method of claim 1 wherein the enlargement sleeve is made of a flexible but substantially inelastic material.

13. The method of claim 1 wherein the enlargement sleeve has a distal portion surrounding the balloon catheter and a proximal portion.

14. The method of claim 13 wherein the positioning step includes the step of manipulating the distal portion using a push rod as the proximal portion.

15. The method of claim 1 further comprising the step of predicting the second diametral dimension based upon the first diametral dimension and the enlargement sleeve selected.

16. The method of claim 1 wherein the enlargement sleeve is sized and constructed to make the second diametral dimension fall within a range of about 110% to 140% of the first diametral dimension.

17. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   selecting a substantially inelastic expandable balloon enlargement sleeve;
   positioning the balloon enlargement sleeve in alignment with the deflated balloon at the target site;
   reinflating the balloon so as to expand the enlargement sleeve therewith at the target site to a second diametral dimension to further dilate the target site; and
   the selecting step including the step of selecting an enlargement sleeve having numerous axial openings formed therein to achieve a desired diametral expansion with the enlargement sleeve.

18. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   selecting an elastomeric, expandable balloon enlargement sleeve;
   positioning the balloon enlargement sleeve in alignment with the deflated balloon at the target site;
   reinflating the balloon so as to expand the enlargement sleeve therewith at the target site to a second diametral dimension to further dilate the target site; and
   the selecting step including the step of selecting a balloon enlargement sleeve having numerous axial openings formed therein to achieve a desired diametral expansion with the enlargement sleeve.

19. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   wherein an elastomeric, expandable balloon enlargement sleeve is disposed on the balloon catheter during at least the inflating and deflating steps;
   positioning the balloon enlargement sleeve in alignment with the deflated balloon while the balloon remains near the target site; and
   reinflating the balloon so as to expand the enlargement sleeve therewith at the target site to a second diametral dimension to further dilate the target site substantially immediately following the positioning step;
   wherein the balloon enlargement sleeve has an initial inside diameter and an initial thickness sized to achieve a desired diametral expansion with the enlargement sleeve.

20. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   wherein an elastomeric, expandable balloon enlargement sleeve is disposed on the balloon catheter during at least the inflating and deflating steps;
   positioning the balloon enlargement sleeve in alignment with the deflated balloon while the balloon remains near the target site;
   reinflating the balloon so as to expand the enlargement sleeve therewith at the target site to a second diametral dimension to further dilate the target site substantially immediately following the positioning step; and
   predicting the second diametral dimension based upon the first diametral dimension and the wall thickness of the enlargement sleeve selected.

21. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   wherein an expandable balloon enlargement sleeve is disposed on the balloon catheter during at least the inflating and deflating steps;
   positioning the balloon enlargement sleeve in alignment with the deflated balloon while the balloon remains near the target site; and
   reinflating the balloon so as to expand the enlargement sleeve therewith at the target site to a second diametral dimension to further dilate the target site substantially immediately following the positioning step;
   wherein the balloon enlargement sleeve is sized and constructed to expand to said second diametral dimension during said reinflating step and further dilate the target site.

22. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   selecting an expandable, elastic balloon enlargement sleeve;
   positioning the balloon enlargement sleeve in alignment with the deflated balloon at the target site;
   reinflating the balloon so as to expand the enlargement sleeve therewith at the target site to a second diametral dimension to further dilate the target site; and
   the selecting step comprising the step of selecting an enlargement sleeve having a wall thickness sufficient to make the second diametral dimension at least about 110% of the first diametral dimension.

23. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   moving the deflated balloon from the target site;
   selecting an expandable balloon enlargement sleeve;
   aligning the enlargement sleeve and the deflated balloon and then moving said aligned enlargement sleeve and deflated balloon to the target site;
   reinflating the balloon so as to expand the enlargement sleeve therewith at the target site to a second diametral dimension to further dilate the target site; end
   the selecting step comprising the step of selecting an enlargement sleeve having a wall thickness sufficient to make the second diametral dimension at least about 110% of the first diametral dimension.

24. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   selecting an expandable balloon enlargement sleeve having a wall thickness of about 0.25 to 0.50 mm when expanded;
   positioning the balloon enlargement sleeve in alignment with the deflated balloon at the target site;
   reinflating the balloon so as to expand the enlargement sleeve therewith at the target site to a second diametral dimension to further dilate the target site; and
   the selecting step comprising the step of selecting an enlargement sleeve having a wall thickness sufficient to make the second diametral dimension at least about 110% of the first diametral dimension.

25. A method for using a balloon catheter comprising the following steps:
   inserting a balloon catheter, of the type including a balloon, into a body lumen;
   aligning the balloon with a target site;
   inflating the balloon to a first diametral dimension to dilate the target site;
   deflating the balloon;
   selecting an expandable balloon enlargement sleeve having numerous axial openings formed therein to facilitate diametral expansion of the enlargement sleeve;
   positioning the balloon enlargement sleeve in alignment with the deflated balloon at the target site;
   reinflating the balloon so as to expand the enlargement sleeve therewith at the target site to a second diametral dimension to further dilate the target site; and
   the selecting step comprising the step of selecting an enlargement sleeve having a wall thickness sufficient to make the second diametral dimension at least about 110% of the first diametral dimension.

26. A method for using a balloon catheter comprising the following steps:
   inserting a balloon catheter, of the type including a balloon, into a body lumen;

aligning the balloon with a target site;

inflating the balloon to a first diametral dimension to dilate the target site;

deflating the balloon;

selecting an expandable balloon enlargement sleeve made of a lubricious material;

positioning the balloon enlargement sleeve in alignment with the deflated balloon at the target site;

reinflating the balloon so as to expand the enlargement sleeve therewith at the target site to a second diametral dimension to further dilate the target site; and the selecting step comprising the step of selecting an enlargement sleeve having a wall thickness sufficient to make the second diametral dimension at least about 110% of the first diametral dimension.

27. A method for using a balloon catheter comprising the following steps:

inserting a balloon catheter, of the type including a balloon, into a body lumen;

aligning the balloon with a target site;

inflating the balloon to a first diametral dimension to dilate the target site;

deflating the balloon;

selecting an expandable balloon enlargement sleeve;

positioning the balloon and the enlargement sleeve relative to one another using radiopaque markers connected to both of the balloon and the balloon enlargement sleeve;

positioning the balloon enlargement sleeve in alignment with the deflated balloon at the target site;

reinflating the balloon so as to expand the enlargement sleeve therewith at the target site to a second diametral dimension to further dilate the target site; and the selecting step comprising the step of selecting an enlargement sleeve having a wall thickness sufficient to make the second diametral dimension at least about 110% of the first diametral dimension.

28. A method for using a balloon catheter comprising the following steps:

inserting a balloon catheter, of the type including a balloon, into a body lumen;

aligning the balloon with a target site;

inflating the balloon to a first diametral dimension to dilate the target site;

deflating the balloon;

selecting an elastomeric, expandable balloon enlargement sleeve;

positioning the balloon enlargement sleeve in alignment with the deflated balloon at the target site;

reinflating the balloon so as to expand the enlargement sleeve therewith at the target site to a second diametral dimension to further dilate the target site;

predicting the second diametral dimension based upon the first diametral dimension and the wall thickness of the enlargement sleeve selected; and wherein the predicting step includes the step of determining if the enlargement sleeve is made of an elastomeric materials and, if so, predetermining an expected reduction in the thickness of the elastomeric material when the balloon is reinflated.

* * * * *